United States Patent [19]
Del Toro

[11] Patent Number: 5,733,267
[45] Date of Patent: *Mar. 31, 1998

[54] PULL BACK STENT DELIVERY SYSTEM

[75] Inventor: Connie Del Toro, Plymouth, Minn.

[73] Assignee: SciMed Life Systems, Inc., Maple Grove, Minn.

[*] Notice: The term of this patent shall not extend beyond the expiration date of Pat. No. 5,571,168.

[21] Appl. No.: 654,559

[22] Filed: May 29, 1996

Related U.S. Application Data

[63] Continuation of Ser. No. 417,385, Apr. 5, 1995, Pat. No. 5,571,168.

[51] Int. Cl.⁶ .................................................... A61M 1/00
[52] U.S. Cl. ................... 604/280; 606/194; 623/1
[58] Field of Search ...................... 604/280, 281, 604/96, 104; 623/1, 11, 12; 606/191, 194, 195, 198, 108

[56] References Cited

U.S. PATENT DOCUMENTS

| | | | |
|---|---|---|---|
| 4,665,918 | 5/1987 | Garza et al. | 128/343 |
| 5,026,377 | 6/1991 | Burton et al. | 606/108 |
| 5,160,341 | 11/1992 | Brenneman et al. | 606/198 |
| 5,201,757 | 4/1993 | Heyn et al. | 606/198 |
| 5,571,168 | 11/1996 | Toro | 623/1 |

FOREIGN PATENT DOCUMENTS 0 627 201 A1  12/1994  European Pat. Off. .

OTHER PUBLICATIONS

"Introducing The First Self–Expanding Large Lumen Biliary Stent . . . ", 1990 Strategic Business Development Inc., pp. 134–137 brochure from Intravascular Stents, Suppliers and Products.

"Wallstent Endoprosthesis—The Expanding Commitment To Innovation", Pfiser Schneider brochure 1992.

"Wallstent Metallic Biliary Endoprosthesis: MR Imaging Characteristics", by Mark J. Girard et al, Sep. 1992, Radiology, pp. 874–877.

"Wallstent Transhepatic Billiary Endoprosthsis With The Unistep Delivery System" brochure, by Pfiser Schneider Mar. 1992.

"Wallstent Endoprosthsis With Unistep Delivery System", by Pfizer Schneider, Jan. 1992.

*Primary Examiner*—John D. Yasko
*Attorney, Agent, or Firm*—Vidas, Arrett & Steinkraus, P.A.

[57] ABSTRACT

A delivery system for implantation of a medical device in a vessel which has three concentric shafts, an inner shaft for carrying a medical device, a middle pull back shaft and an outer stiffening shaft. The inner and outer shafts are connected together at the proximal end of the delivery system to preclude the inner shaft from moving axially relative to the outer shaft as the middle pull back shaft is retracted. This allows for accurate placement of the medical device.

8 Claims, 6 Drawing Sheets

PULL BACK STENT DELIVERY SYSTEM

This application is a continuation of application Ser. No. 08/417,385, filed Apr. 5, 1995, which is now U.S. Pat. No. 5,571,168.

BACKGROUND OF THE INVENTION

1. Field of the Invention

The present invention relates to an improved delivery system for delivering and deploying a medical device, such as a stent. More specifically, the invention relates to a delivery system for more accurate placement of a medical device such as a stent when using a pull back delivery system.

2. Description of the Related Art

Stents and delivery systems for deploying stents are highly developed and well known field of medical technology. Stents have many well known uses and applications. A stent is a prosthesis which is generally tubular and which is expanded radially in a vessel or lumen to maintain its patency. Stents are widely used in body vessels, body canals, ducts or other body lumens.

Stents, stent-grafts and the like are commonly delivered using a catheter delivery system. A common type of delivery system for delivering a self-expanding stent is called a pull back delivery system. This type of delivery system utilizes two catheters or shafts which are concentrically arranged, one around another. The stent is carried axially around the distal end of the inner catheter or shaft. The stent is carried to the delivery site on the distal end of the delivery device, held in its compressed delivery position by the outer shaft or catheter. Once at the desired placement site, the outer shaft is pulled back, releasing the stent to self-expand.

In testing, applicant's have observed that the portion of the catheter outside the body is typically not straight, but is curved during pull back. The frictional forces caused by pulling back the outer catheter or shaft cause the curve of the entire device to flatten out, which causes the distal end of the inner shaft or catheter to be urged forward. This undesired forward movement of the inner shaft often leads to inaccurate placement of the stent.

Another factor which can lead to placement inaccuracy are curves inside the body. A common and well known type of delivery is a contralateral insertion approach, where the distal end of the delivery device is placed on the opposite illiac from the original insertion site. In this case, the pull back delivery systems can also cause the curve placed inside the illiac vessels to straighten out or flatten slightly as the outer catheter or shaft is pulled back. This also causes undesired forward movement of the inner shaft, which can lead to inaccurate placement of the stent.

Schneider's WALLSTENT® product with Unistep™ delivery system utilizes a stainless steel tube as the inner shaft for the portion of the delivery system outside the body, and a plastic flexible tube as the inner shaft inside the body. The stainless steel tube prevents the proximal end of the device from curving outside the body. This device prevents placement error from the curve flattening out outside the body, but does not prevent placement error from a curve flattening out inside the body. Also, the Schneider approach may require different lengths of stainless steel tubing depending on the type of procedure, such as an ipsilateral femoral artery insertion versus a contralateral insertion, or a biliary duct insertion.

There remains a need in the art for a stent delivery system which prevents axial movement of one catheter shaft from causing forward movement of the other catheter shaft, which will allow for accurate placement of a medical device.

SUMMARY OF THE INVENTION

The inventive delivery device includes a catheter which is comprised of three concentric shafts. A medical device such as a self-expanding stent is held in a reduced delivery configuration for insertion and transport through a body lumen to a predetermined site for deployment. The stent is carried axially around the inner shaft and is held in its reduced delivery configuration by the middle shaft. An outer shaft is used to stiffen the delivery device so that the arc of the inner shaft will not change outside of the body when the middle shaft is pulled back to release the stent to self-expand. The outer shaft is connected to the inner shaft at the proximal end of the device, which stiffens the delivery system so that the inner shaft will not be urged forward as the middle shaft is pulled backward.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
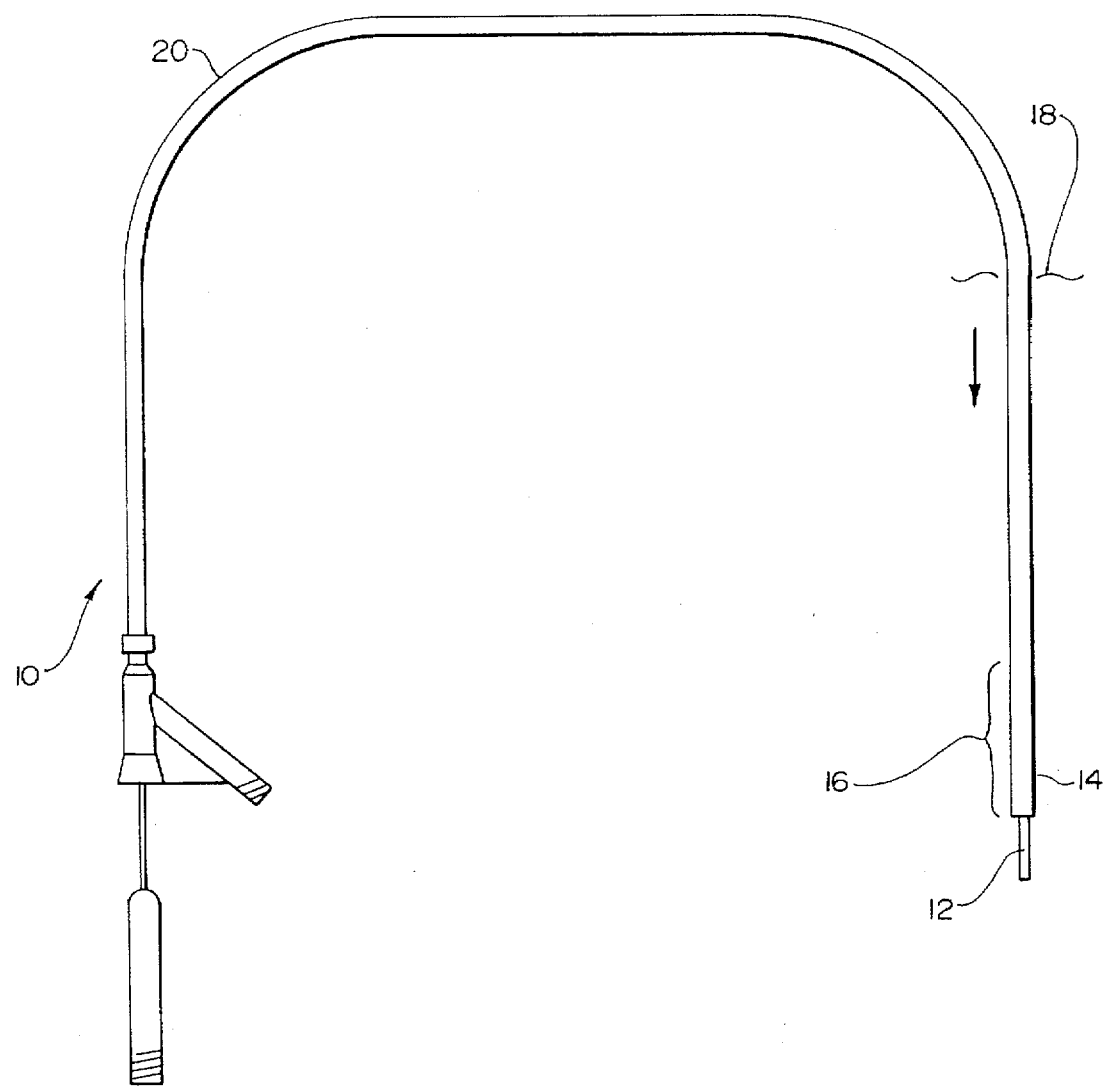
FIG. 1 is a prior art delivery device having two shafts concentrically arranged and with an arc outside the body.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows a prior art stent delivery system, shown generally at 10, which is comprised of two concentrically arranged catheters, shafts or manifolds. The inner shaft is shown at 12 and the outer shaft is shown at 14. A medical device such as a self-expanding stent (not shown) is carried axially around the inner shaft 12 and is held in its reduced delivery configuration by the outer shaft 14. The stent is carried near the distal end 16 of the delivery system 10. Reference numeral 18 shows schematically the separation between the portion of the device which is outside the body and the portion of the device which is inside the body. Reference numeral 20 shows the arc outside the body prior to deployment of the stent.

Figure 2:
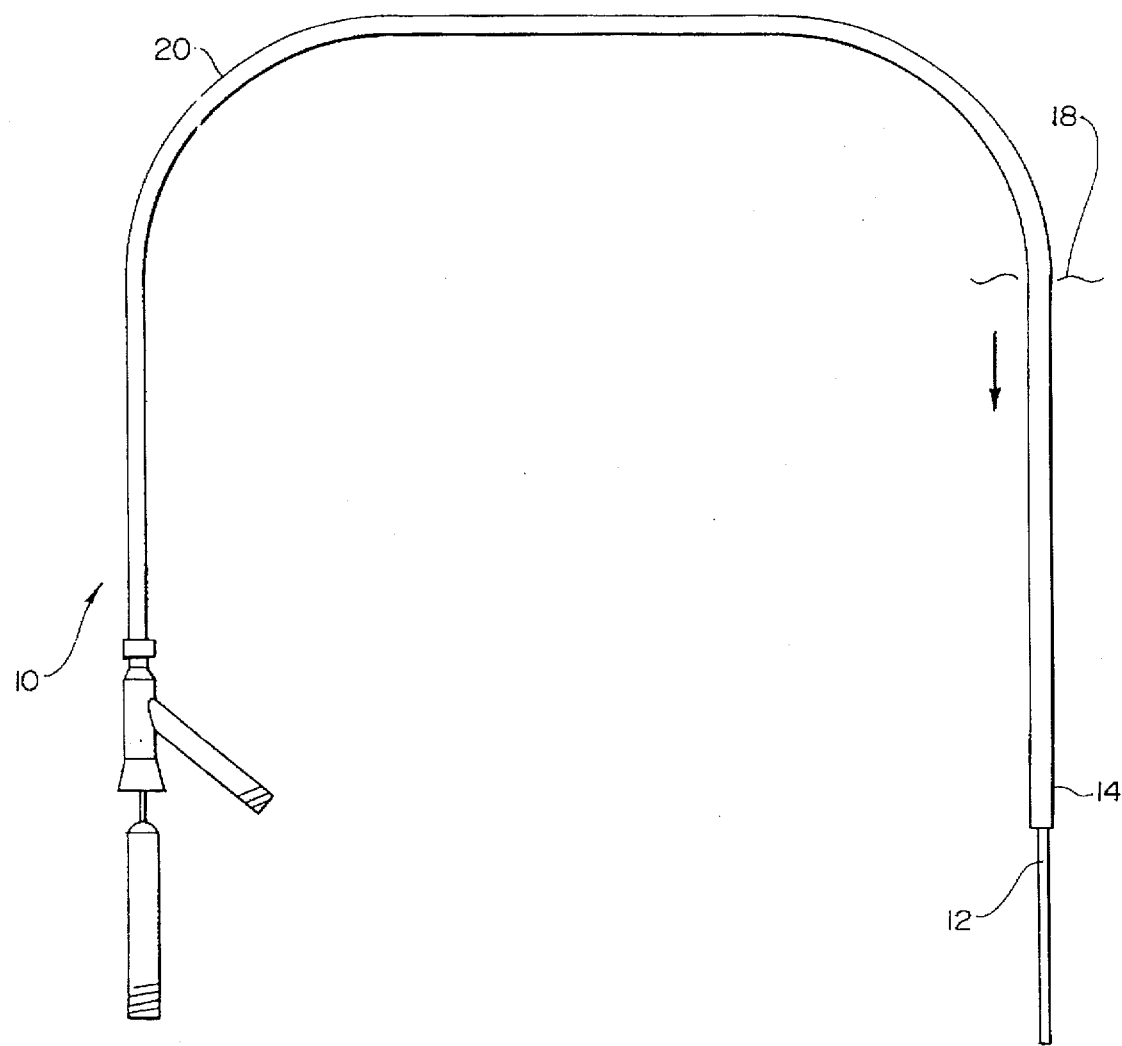
FIG. 2 shows the arc outside the body of the prior art delivery device of FIG. 1 flattening out as the outer shaft or catheter is pulled back to release the stent.

FIG. 2 shows the prior art device of FIG. 1 after the outer manifold or shaft has been pulled back to allow the stent to self-expand and deploy. FIG. 2 shows that arc 20 has flattened out as the outer shaft 14 is pulled back and inner shaft 12 moves forward.

Figure 3:
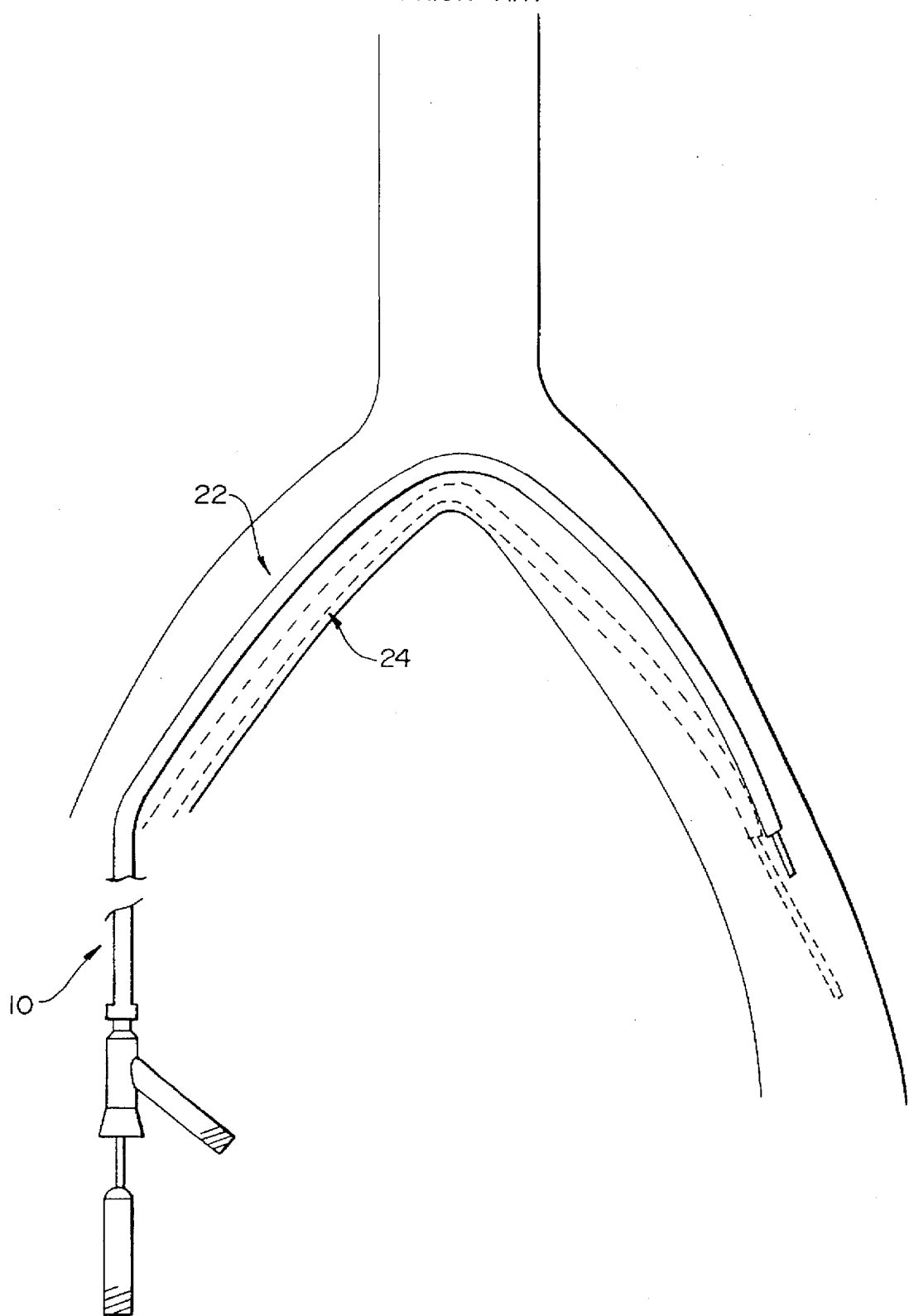
FIG. 3 shows the arc inside the body of a prior art delivery device during a contralateral insertion, with the flattening of the arc during deployment shown in silhouette.

FIG. 3 shows the distal end of a prior art device during a contralateral insertion. As the medical device is deployed, the arc at 22 flattens out from its predeployment position to its deployed position, shown in silhouette at 24.

Figure 4:
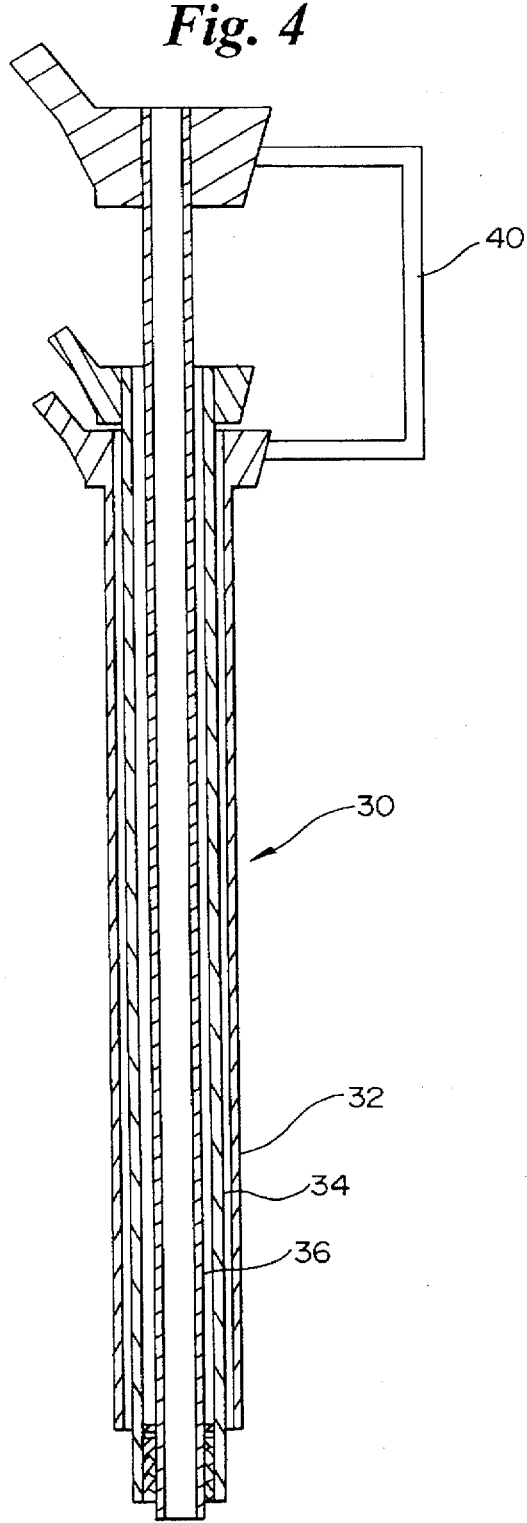
FIG. 4 is a sectional view of the inventive delivery system, showing the stent undeployed.
Figure 5:
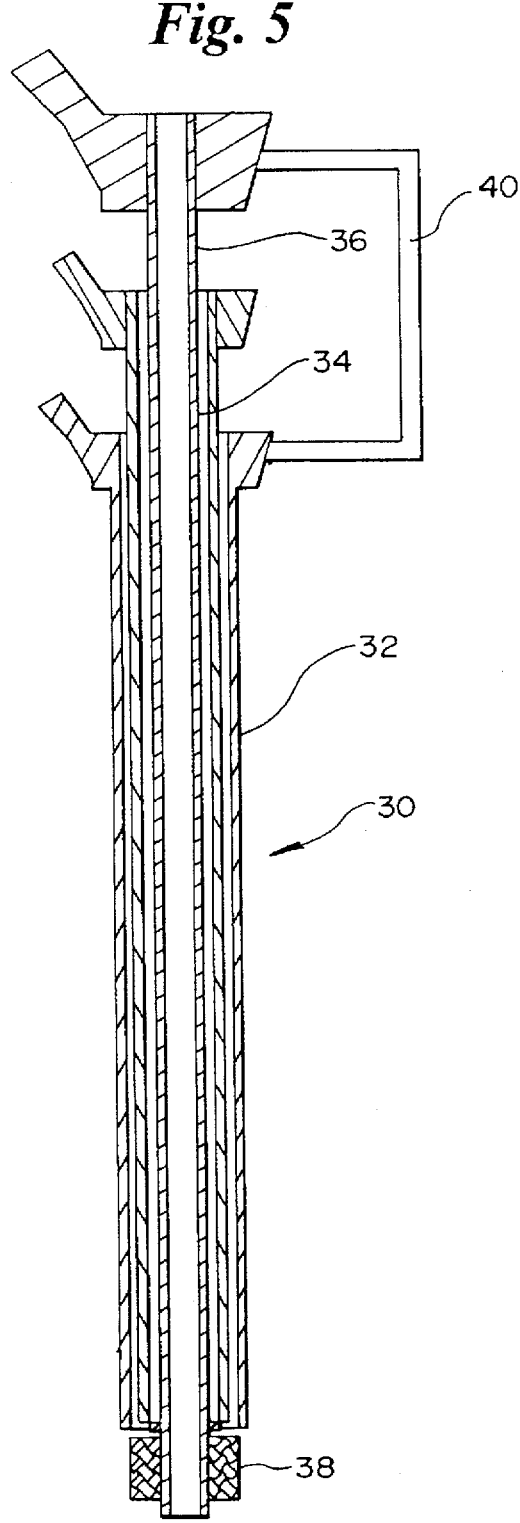
FIG. 5 is a sectional view of the inventive delivery system of FIG. 3, showing the stent deployed.

Referring now to FIGS. 4 and 5, the inventive deployment system is shown schematically and generally referred to as 30. The outer stiffening shaft is referred to at 32, the middle pull back shaft is referred to at 34 and the inner shaft is referred to at 36. The inner shaft 36 can function as the lumen for a guide wire. A medical device, such as self-expanding stent 38 is shown in the delivery position in FIG. 4, carried axially around inner shaft 36 and held in its reduced delivery configuration by middle pull back shaft 34. The outer shaft 32 and inner shaft 36 are connected together by manifold stabilizer 40 at the proximal end of the device. It is important that the two shafts are connected together far enough apart to provide enough room for the middle pull back shaft to be fully retracted to completely release the stent 38 to self-expand, as shown in FIG. 5. By connecting the outer shaft 32 and the inner shaft 36 with manifold stabilizer 40, the inner shaft 36 is held in position during pull back of the middle pull back shaft 34, thereby preventing any flattening of the outside the body arc or the inside the body arc during deployment. The inventive delivery system provides for accurate placement of the medical device.

Figure 6:
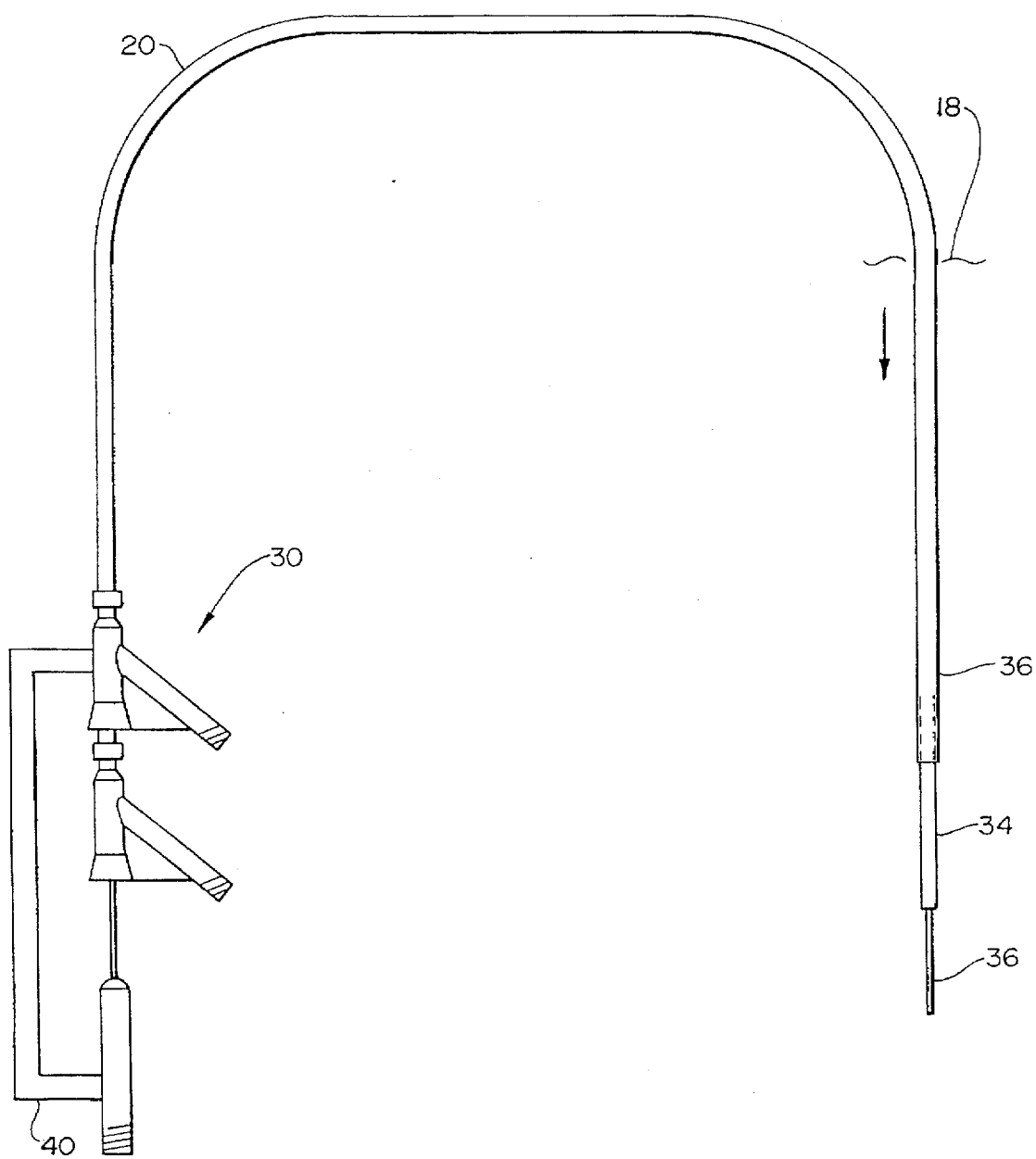
FIG. 6 schematically shows the arc outside the body of the inventive delivery system with the stent undeployed, and FIG. 7 schematically shows the arc unchanged outside the body of the inventive delivery system with the stent deployed.
Figure 7:
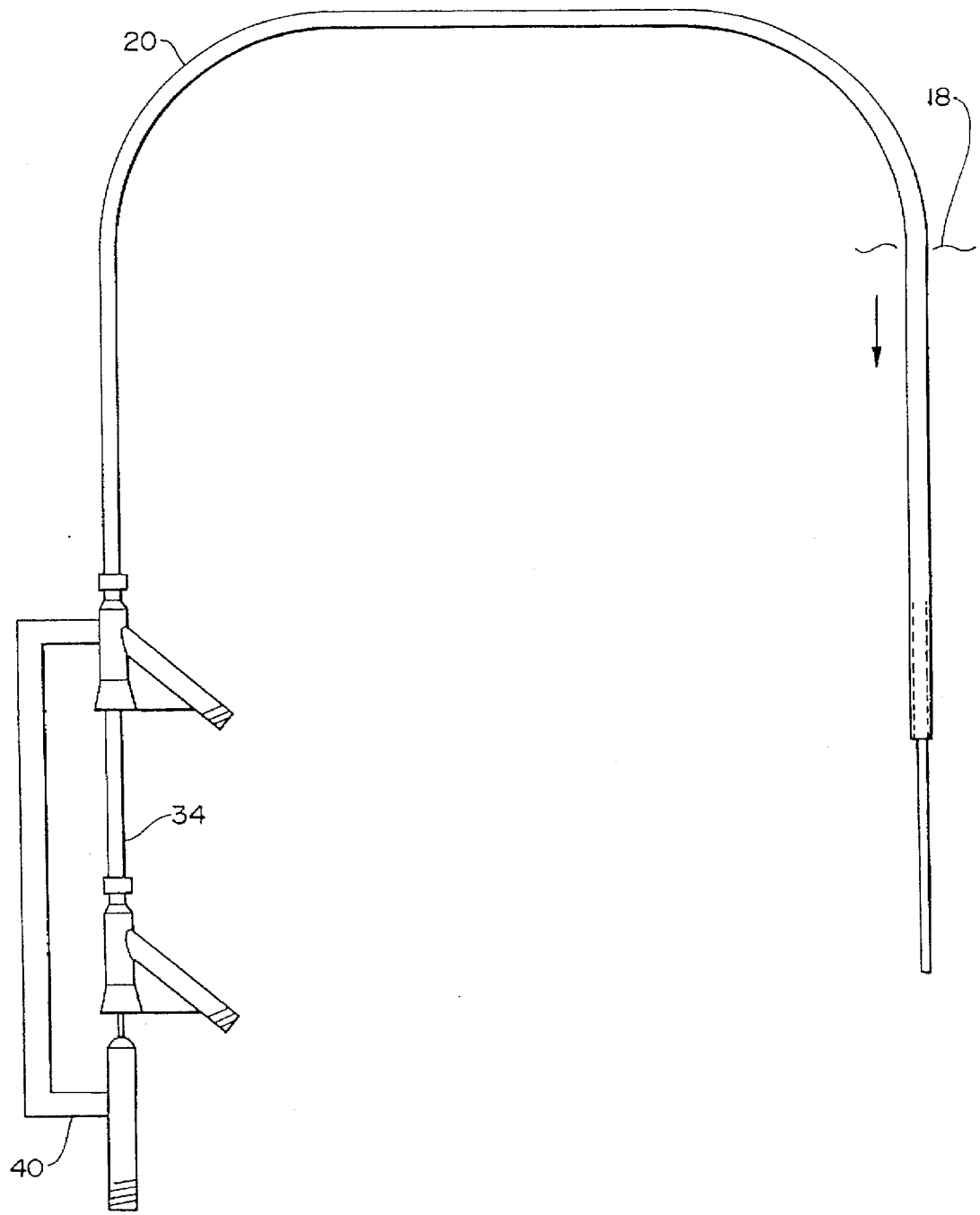

Referring now to FIGS. 6 and 7, the inventive delivery device 30 is shown prior to deployment and after deployment. FIG. 7 shows that the manifold stabilizer 40 prevents any flattening of arc 20 as middle pull back shaft 34 is retracted to allow the stent 38 to self-expand (shown in FIG. 5). Similarly, the inventive delivery device will prevent any flattening of the arc inside the body, shown in FIG. 3, during a contralateral insertion.

This completes the description of the preferred and alternate embodiments of the invention. It is to be understood that even though numerous characteristics and advantages of the present invention have been set forth in the foregoing description, together with the details of the structure and function of the invention, the disclosure is illustrative only and changes may be made in detail, especially in matters of shape, size and arrangement of parts within the principals of the invention, to the full extent indicated by the broad, general meaning of the terms in which the appended claims are expressed. Those skilled in the art may recognize other equivalents to the specific embodiment described herein which are intended to be encompassed by the claims attached hereto.

What is claimed is:

1. A delivery system for implantation of a medical device in a vessel, comprising:
   a medical device; and
   an elongate flexible catheter means having proximal and distal ends for delivering a medical device to a predetermined location in a vessel of a patient, the elongate flexible catheter means being further comprised of:
      an inner shaft which carries the medical device near its distal end;
      a middle pull back shaft concentrically arranged around the inner shaft; and
      an outer stiffening shaft concentrically arranged around the middle pull back shaft, the inner and outer shafts being permanently connected at their proximal ends to prevent any axial movement of the inner shaft with respect to the outer shaft such that the shafts constitute a single delivery catheter, wherein the middle pull back shaft is retracted relative to the inner shaft and the stiffening shaft to deploy the medical device.

2. The delivery system of claim 1, wherein the inner and outer shafts are connected together far enough apart to allow the middle pull back shaft to retract a distance at least as great as the axial length of the medical device to be delivered.

3. The delivery system of claim 1, wherein the inner shaft provides a lumen for a guide wire.

4. The delivery system of claim 1 wherein the medical device is a self-expanding stent.

5. A method of delivering a medical device using the delivery system of claim 1, comprising the steps of:
   moving the distal end of the elongate flexible catheter means to a delivery site, and
   delivering the medical device by pulling back on the middle pull back shaft which releases the medical device,
   whereby the outer stiffening shaft connection to the inner shaft prevents the distal end of the inner shaft from being urged forward as the middle pull back shaft is retracted, thereby allowing for more accurate placement of the medical device.

6. A delivery system for implantation of a medical device in a vessel, comprising:
   a medical device; and
   an elongate flexible catheter means having proximal and distal ends for delivering a medical device to a predetermined location in a vessel of a patient, the elongate flexible catheter means being further comprised of:
      an inner shaft which carries the medical device near its distal end;
      a middle pull back shaft concentrically arranged around the inner shaft; and
      an outer stiffening shaft concentrically arranged around the middle pull back shaft, the inner and outer shafts being irremovably connected at their proximal ends such as to constitute a one piece single delivery catheter to prevent axial movement of the inner shaft with respect to the outer shaft, wherein the middle pull back shaft is retracted relative to the inner shaft and the stiffening shaft to deploy the medical device.

7. A delivery system for implantation of a medical device in a vessel, comprising:
   a medical device; and
   an elongate flexible catheter means having proximal and distal ends for delivering a medical device to a predetermined location in a vessel of a patient, the elongate flexible catheter means being further comprised of:
      an inner shaft;
      a middle pull back shaft concentrically arranged around the inner shaft, whereby the medical device may be carried between the inner shaft and middle pull back shaft; and
      an outer stiffening shaft concentrically arranged around the middle pull back shaft;
      an manifold stabilizer irremovably connected to both the inner and outer shafts, the inner and outer shafts as a result being connected such as to constitute a one piece construction in order to prevent any axial movement of the inner shaft with respect to the outer shaft such that the shafts constitute a single delivery catheter, wherein the middle pull back shaft is retracted relative to the inner shaft and the stiffening shaft by pulling on the proximal end of the middle pull back shaft, and wherein the outer stiffening shaft connection to the inner shaft prevents axial movement of the inner shaft with respect to the outer stiffening shaft (32).

8. A stent delivery system comprising:

a catheter and a stent carried by the catheter;

cover means surrounding the stent and constructed and arranged for retraction to expose the stent for release from the catheter;

the catheter being constructed and arranged to receive at least part of the cover means interiorly thereof upon retraction of the cover means.

* * * * *